United States Patent
Chaudhary

(12) 
(10) Patent No.: US 11,471,422 B2
(45) Date of Patent: Oct. 18, 2022

(54) STEALTH, TARGETED NANOPARTICLES (STN) FOR ORAL DRUG DELIVERY

(71) Applicant: Manu Chaudhary, Panchkula (IN)

(72) Inventor: Manu Chaudhary, Panchkula (IN)

(*) Notice: Subject to any disclaimer, the term of this patent is extended or adjusted under 35 U.S.C. 154(b) by 839 days.

(21) Appl. No.: 15/514,333

(22) PCT Filed: Sep. 22, 2015

(86) PCT No.: PCT/IN2015/050114
§ 371 (c)(1),
(2) Date: Mar. 24, 2017

(87) PCT Pub. No.: WO2016/046845
PCT Pub. Date: Mar. 31, 2016

(65) Prior Publication Data
US 2017/0281559 A1  Oct. 5, 2017

(30) Foreign Application Priority Data

Sep. 25, 2014 (IN) .......................... 2752/DEL/2014

(51) Int. Cl.
| | |
|---|---|
| *A61K 9/51* | (2006.01) |
| *A61K 45/06* | (2006.01) |
| *A61K 47/55* | (2017.01) |
| *A61K 47/69* | (2017.01) |
| *A61K 9/00* | (2006.01) |
| *A61K 31/122* | (2006.01) |
| *A61K 31/202* | (2006.01) |
| *A61K 31/337* | (2006.01) |
| *A61K 31/407* | (2006.01) |
| *A61K 31/4164* | (2006.01) |
| *A61K 31/43* | (2006.01) |
| *A61K 31/436* | (2006.01) |
| *A61K 31/4439* | (2006.01) |
| *A61K 31/519* | (2006.01) |
| *A61K 31/5383* | (2006.01) |
| *A61K 31/546* | (2006.01) |
| *A61K 31/7036* | (2006.01) |
| *A61K 31/7048* | (2006.01) |
| *A61K 31/714* | (2006.01) |
| *A61K 38/05* | (2006.01) |
| *A61K 38/12* | (2006.01) |
| *A61K 38/14* | (2006.01) |

(52) U.S. Cl.
CPC .......... *A61K 9/5161* (2013.01); *A61K 9/0053* (2013.01); *A61K 9/5123* (2013.01); *A61K 9/5146* (2013.01); *A61K 31/122* (2013.01); *A61K 31/202* (2013.01); *A61K 31/337* (2013.01); *A61K 31/407* (2013.01); *A61K 31/4164* (2013.01); *A61K 31/43* (2013.01); *A61K 31/436* (2013.01); *A61K 31/4439* (2013.01); *A61K 31/519* (2013.01); *A61K 31/5383* (2013.01); *A61K 31/546* (2013.01); *A61K 31/7036* (2013.01); *A61K 31/7048* (2013.01); *A61K 31/714* (2013.01); *A61K 38/05* (2013.01); *A61K 38/12* (2013.01); *A61K 38/14* (2013.01); *A61K 45/06* (2013.01); *A61K 47/551* (2017.08); *A61K 47/6939* (2017.08)

(58) Field of Classification Search
CPC .... A61K 9/5161; A61K 31/714; A61K 38/12; A61K 9/0053; A61K 9/5123; A61K 31/122; A61K 31/202; A61K 31/337; A61K 31/407; A61K 31/4164; A61K 31/43; A61K 31/436; A61K 31/4439; A61K 31/519; A61K 31/5383; A61K 31/546; A61K 31/7036; A61K 31/7048; A61K 38/14; A61K 38/05; A61K 47/6939; A61K 47/551; A61K 45/06; A61K 9/5146
See application file for complete search history.

(56) References Cited

U.S. PATENT DOCUMENTS

| | | | |
|---|---|---|---|
| 6,998,393 B2 * | 2/2006 | Jin ....................... | A61K 9/0043 424/489 |
| 2003/0124189 A1 * | 7/2003 | Zentner ................ | A61K 9/2031 424/486 |

(Continued)

OTHER PUBLICATIONS

Ganguly, Kuntal et al., "Polysaccharide-based micro/nanohydrogels for delivering macromolecular therapeutics", Journal of Controlled Release, Elsevier, Amsterdam, vol. 193, May 17, 2014, 162-173, XP029084262, abstract, p. 162, right-hand column, paragraph 3, p. 163, left-hand column, paragraph 1, p. 164, left-hand column, paragraph 3-6, p. 170, right-hand column & paragraph 1.

Sampath C. Abey Lath et al., "Click synthesis of dextran macrostructures for combinatorial-designed self-assembled nanoparticles encapsulating diverse anticancer therapeutics", Bioorganic & Medicinal Chemistry, Pergamon, GB, vol. 19, No. 21, pp. 6167-6173, XP028316306, Sep. 13, 2011, 6167-6173, XP028316306, p. 6168, right-hand column p. 6172-p. 6173.

(Continued)

*Primary Examiner* — Matthew P Coughlin
*Assistant Examiner* — Thurman Wheeler
(74) *Attorney, Agent, or Firm* — Lombard & Geliebter LLP; Eric J. Huang, Esq.

(57) ABSTRACT

The present invention relates to a technology for oral delivery of Poorly Bio-Available Therapeutic Agents and the formulations derived using this technology. Poorly Bio-Available Therapeutic Agents may belong to BCS class III/IV drugs or nutraceutical or any other agent which is required to be orally delivered having challenge of bio-availability in body. Therefore, invention further relates to a targeted delivery technology for enhanced bio-availability and controlled release without being degraded. The present invention further relates to the processes for the preparation of said compositions and formulations made thereof. The formulations of the present invention are useful to treat related conditions.

19 Claims, 7 Drawing Sheets

(56) References Cited

U.S. PATENT DOCUMENTS

| | | | | |
|---|---|---|---|---|
| 2006/0205682 A1* | 9/2006 | Roberts | ............... | A61K 31/505 |
| | | | | 514/28 |
| 2009/0004118 A1* | 1/2009 | Nie | ..................... | A61K 47/551 |
| | | | | 424/9.35 |
| 2009/0252803 A1 | 10/2009 | Yuan et al. | | |
| 2013/0157992 A1* | 6/2013 | Latham | ............... | A61K 9/2031 |
| | | | | 514/179 |

OTHER PUBLICATIONS

Singh, Amit et al., "Combinatorial approach in the design of multifunctional polymeric nano-delivery systems for cancer therapy", Journal of Materials Chemistry B, vol. 2, No. 46, Jan. 1, 2014, pp. 8069-8084, XP55240623, p. 8078, left-hand column, lines 6-7, paragraph 1, p. 8078, left-hand column, paragraph 2.

Wu, Fei et al., "Development of dextran nanoparticles for stabilizing delicate proteins", Nanoscale Research Letters, Dec. 1, 2013, pp. 1-8, XP55241159, p. 3, last paragraph p. 7, right-hand column.

Soliveira, Michele F. et. al., "Strategies to target tumors using nanodelivery systems based on biodegradable polymers, aspects of intellectual property, and market", Journal of Chemical Biology, Springer-Verlag, Berlin/Heidelberg, vol. 6, No. I, Nov. 30, 2012, pp. 7-23, XP035158850, p. 11, right-hand column, paragraph 1.

International Search Report of PCT/IN2015/050114, dated Mar. 31, 2016.

\* cited by examiner

STEALTH, TARGETED NANOPARTICLES (STN) FOR ORAL DRUG DELIVERY

RELATED APPLICATIONS

This application is a national phase of PCT/IN2015/050114, filed on Sep. 22, 2015 which claims priority to 2752/DEL/2014 filed Sep. 25, 2014. The content of those applications are hereby incorporated by reference.

FIELD OF THE INVENTION

The present invention relates to technology for oral delivery of Poorly Bio-available Therapeutic Agents (PBTA) and their method of preparation. Particularly, the invention relates to targeted delivery of therapeutic agents using Stealth Targeted Nanoparticle (STN) technology. More particularly the invention relates to method of delivery of BCS class III and class IV drugs or poorly permeable nutraceutical agents directly at target site without being degraded or macrophaged for controlled delivery of said therapeutic agent using green chemistry approach.

BACKGROUND OF THE INVENTION

Oral route is the most commonly used and preferred route of administration but bio-availability remains a challenge for some therapeutic agents particularly for BCS class III & IV drugs and other poorly permeable nutraceutical agents. These drugs/nutraceutical agents exhibit a high variation in the rate and extent of absorption.

Water-soluble drugs including physiological active agents, protein drugs, have low stability in the gastrointestinal tract and low permeability to the wall of intestinal tract, and thus intravenous injection has been usually used for these drugs. At the same time poorly soluble agents are usually entrapped in lipids or oil emulsions and have limitations of their rapid clearance from circulation due to uptake by reticulo-endothelial system (RES), primarily in the liver. The major challenge in the oral drug delivery is the development of novel dosage forms to endorse absorption of poorly permeable drugs across the intestinal epithelium. In order to deliver these drugs via the oral route, the epithelial barrier of the intestine has to be perturbed in a safe, reversible and reproducible manner. New attention directed to this area in recent years is due to the better understanding of the dynamic regulation of tight junction permeability.

Patent EP20100749385, discloses an oral formulation that inhibits degradation of the bioactive compound within the stomach and within the lumen of the intestine by encapsulation within a polymeric shell, preventing its dissolution until after passing through the mucosal wall of the small and/or large intestine. Enzymatic degradation of the delivery vehicle containing the bioactive compound is substantially inhibited (resisted) until after absorption of the delivery vehicle into blood vessels of the intestinal mucosa. This patent has limitation of being complicated and requires covalent conjugation. Some of the other techniques used in recent past are liposomal preparations, lipid polymer bilayers formation, use of bio-erodible muco-adhesive polymers to avoid first pass metabolism, coating to avoid peptic degradation and formation of nanoparticles.

Patent AU 2004/305395 B2 discloses orally administrable nanoparticle compositions having enhanced (70%) entrapping rate of water-soluble drugs within nanoparticles composed of lipids and polymers, and being stable against lipases, wherein the nanoparticles are prepared by binding water-soluble drugs with counter-ion substances and adding lipids, polymers, and emulsifiers thereto. The major limitation is they are unstable, have slow drug release and danger of being phagocytosed. Solid lipid nanoparticles (SLN) have problems of particle aggregation and physical stability.

It is a well known fact that the rate of dissolution of a particulate agent can be increased by decreasing particle size. This has been achieved and reported in previous patents by one or more of micro fluidizing technique, milling, micronization, nanosizing, crystal engineering, solid dispersions, cyclodextrins, solid lipid nanoparticles and other colloidal drug delivery systems such as microemulsions, self-emulsifying drug delivery systems, self-microemulsifying drug delivery systems, liposomes and use of permeation enhancer. Over the last few decades, nanocarriers for drug delivery have emerged as powerful tools with unquestionable potential to improve the therapeutic efficacy of anti-cancer drugs. By virtue of their small size they are injected intravenously and disposed into the target tissues where they release the drug. Nanocarriers interact massively with the surrounding environment, namely, endothelium vessels as well as cells and blood proteins. Consequently, they are rapidly removed from the circulation mostly by the mononuclear phagocyte system.

At the same time active agent levels are to be maintained within therapeutic plasma concentration, but in order to achieve this larger doses of conventionally formulated dosage forms are required to be administered. This approach is unsafe as it produces toxic effects due to high plasma concentration of the drug. Alternatively, another approach is to administer a drug at certain intervals of time, resulting in fluctuating drug levels, the so-called peak and valley effect. This approach is generally associated with several potential problems, such as a large peak (toxic effect) and valley (non-active drug level) effect, and a lack of patient compliance leading to drug therapy inefficiency or failure.

There are many contributing factors which can affect the oral bio-availability of drugs in the gastrointestinal tract including thickness of the epithelium, the surface area, blood flow and local physical and chemical environment, characteristics of the drug substance itself, such as its solubility in water, its chemical stability, molecular weight and particle size. However, before a bioactive compound is transferred from the intestinal lumen to the blood, the compound may be subject to degradation or deactivation by the various components of the lumen.

Though each of the above described systems and others are somewhat effective in delivering poorly bio-available drugs through the mucosal membrane after oral delivery, each have drawbacks that prevent their widespread use. Some of the compositions and/or methods do not provide significant concentrations (<30%) through the mucosal membrane and as such limit their functionality. Additionally, other compositions and/or methods of mucosal delivery are too costly. For example, orally administrable formulations for water-soluble drugs using w/o or w/o/w emulsion, or liposome are known in the art. However, they have drawbacks of having insufficient drug entrapping rate and low stability.

There is thus still a need for alternative oral drug delivery for poorly bio available agents with improved intestinal absorption.

OBJECTS OF THE INVENTION

It is an objective of one of the embodiment of the present invention to provide a novel technology for oral delivery of poorly bio-available therapeutic agents (PBTA).

It is another objective of current invention to disclose a novel stealth targeted nanoparticle technology for targeted delivery of poorly bio-available therapeutic agents.

It is an objective of the one of the embodiment of the present invention to provide oral nanoparticle compositions and method of preparation of poorly bio-available therapeutic agents (BCS class III and BCS class IV drugs/poorly permeable nutraceuticals) and their combination thereof using Stealth Targeted Nanoparticles (STN) Technology.

It is an objective of the one of the embodiment of the present invention to provide oral stealth targeted nanoparticle compositions wherein therapeutically effective amount of Poorly Bio-Available Therapeutic Agents (drugs/nutraceuticals) are combined with a stealth polymer matrix along with a non protein targeting agent to target the receptors.

It is an objective of the one of the embodiment of the present invention to provide stealth targeted nanoparticles technology and compositions made thereof of poorly bio-available therapeutic agents (BCS class III and BCS class IV drugs)/nutraceuticals wherein the oral bio-availability of these nanoparticles is significantly enhanced in comparison to prior arts, conventionally available forms.

It is an objective of the one of the embodiment of the present invention to provide poorly bio-available therapeutic agents (drugs/nutraceuticals) directly at target site without being degraded.

Another objective of the one of the embodiment of the present invention is to provide method of manufacture of the Stealth Targeted Nanoparticles (STN) of poorly bio-available therapeutic agents using green chemistry approach.

Still another object of the one of the embodiment of the present invention is to provide enhanced efficacy of the stealth targeted nanoparticles of poorly bio-available drugs/nutraceuticals due to enhanced loading of higher drug concentrations.

It is an object of the invention to provide the advantages of improved bio-availability of the drug molecule and reduction in number of side effects due to targeted delivery and controlled release.

SUMMARY OF THE INVENTION

In view of the forgoing, stealth targeted nanoparticles of poorly bio-available therapeutic agents (BCS class III and BCS class IV drugs/nutraceuticals) are described for oral delivery and for the treatment of related conditions. The formulation/composition comprises an effective amount of one or more poorly bio-available therapeutic agent (PBTA) combined within a water soluble polymer matrix with a non protein targeting agent to target the receptor to obtain maximum therapeutic effects.

In another aspect, the formulation of stealth targeted nanoparticles of poorly bio-available therapeutic agents (BCS class III and BCS class IV drugs/nutraceuticals) are in oral form which may be a tablet or capsule or sachet or any other NDDS form known to a person skilled in the art.

In another aspect a method of preparation of the stealth targeted nanoparticles of poorly bio-available therapeutic agents (BCS class III and BCS class IV drugs/nutraceuticals) alone or in combination is provided using semi inter penetrating network of polymers and targeting ligand using green chemistry approach.

In yet another aspect a method of use of the stealth targeted nanoparticles of poorly bio-available therapeutic agents (BCS class III and BCS class IV drugs/nutraceuticals) is provided.

In another aspect, a method of treatment using the stealth targeted nanoparticles of poorly bio-available therapeutic agents (BCS class III and BCS class IV drugs/nutraceuticals) is provided.

BRIEF DESCRIPTION OF THE DRAWINGS

The embodiments herein will be better understood in terms of their characteristics and effectiveness from the following detailed description with reference to the figures depicting various test results.

Figure 1:
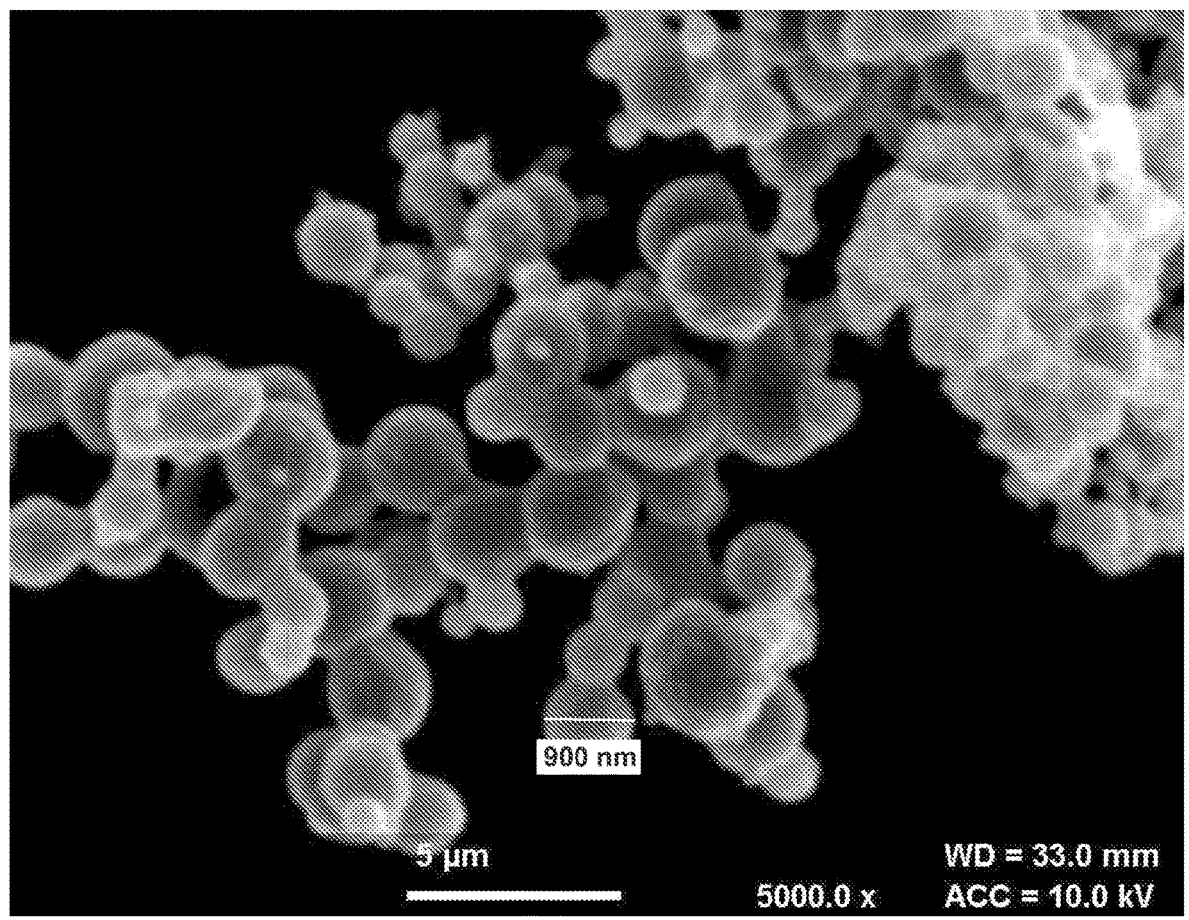
FIG. 1: Scanning electron microscopy of spray dried STN (5000×) showing particles are spherical in nature with homogeneous characteristics and smooth appearance.
Figure 2:
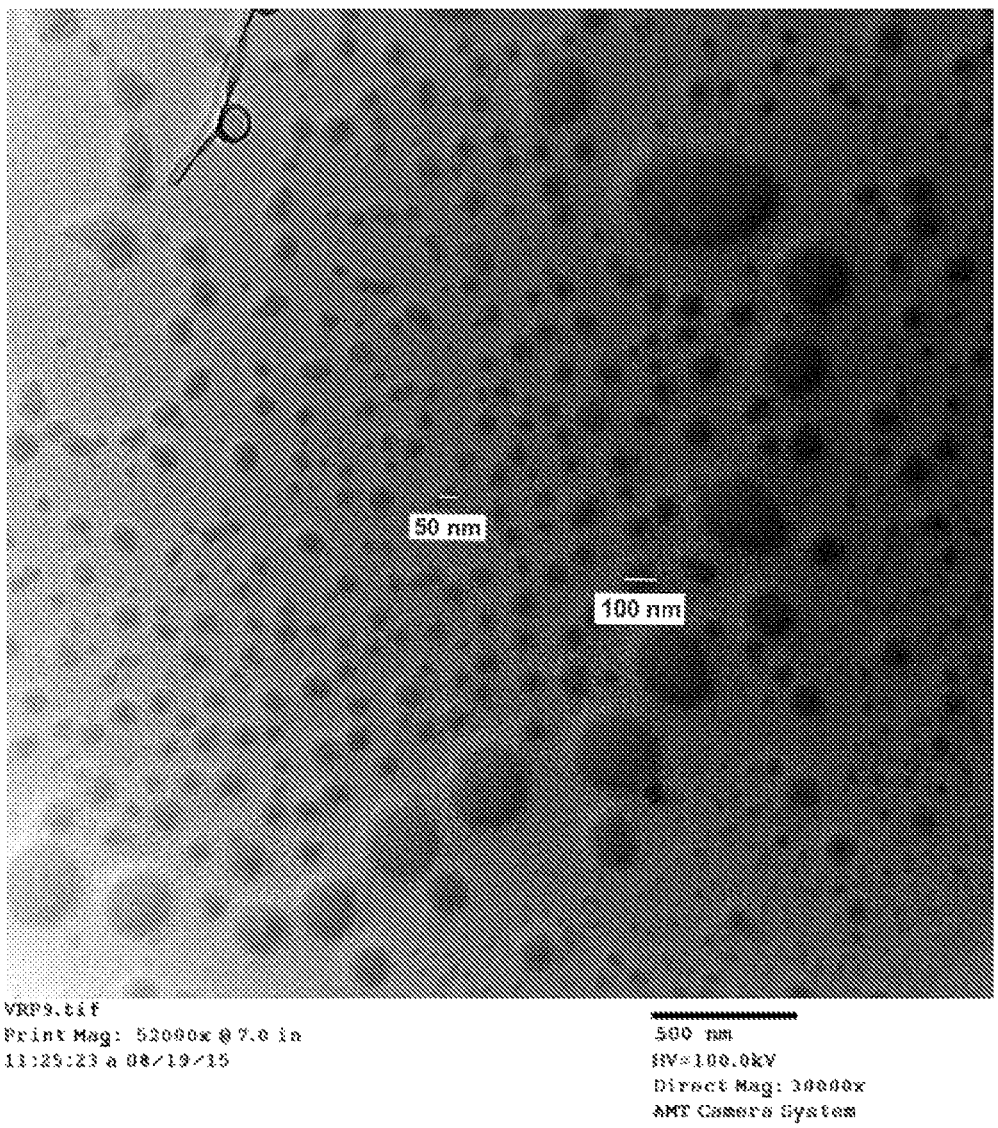
FIG. 2: Transmission electron microscopy of STN at 30000× showing swelling and bursting into smaller size nanoparticles.
Figure 3:
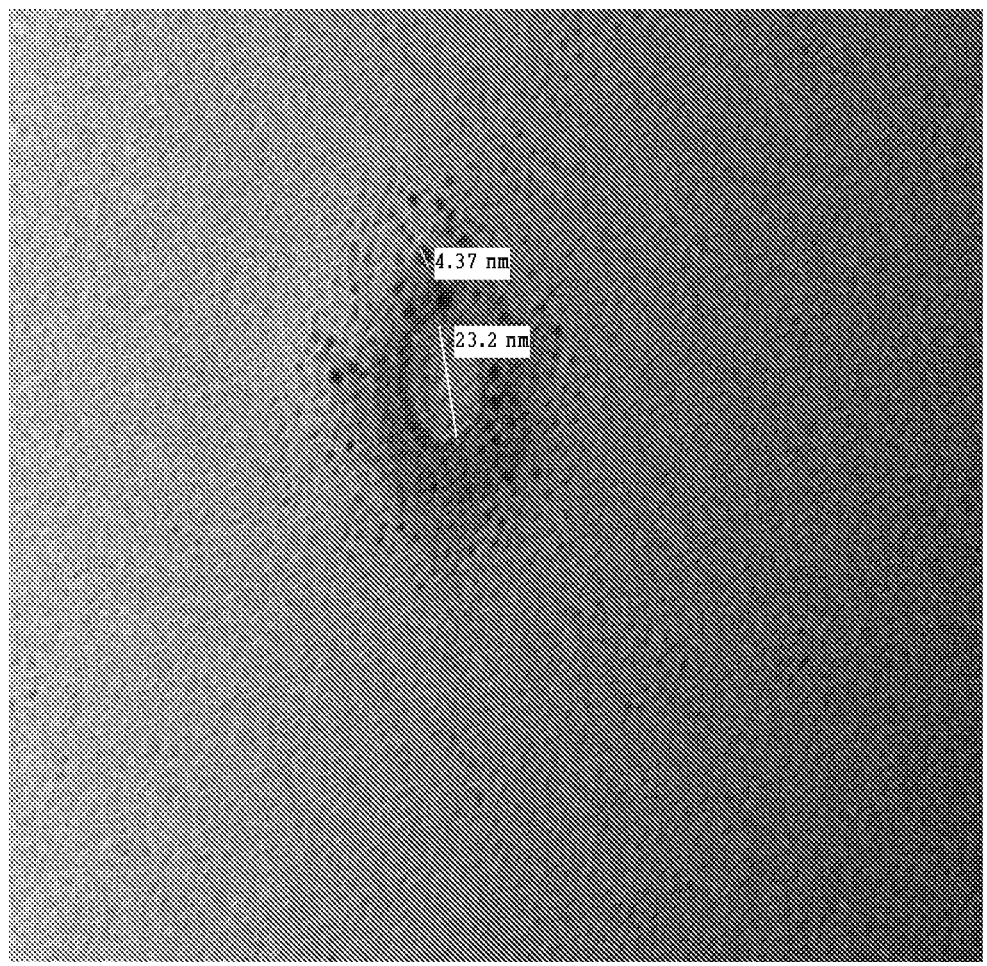
FIG. 3: Transmission electron microscopy of STN at 40000× showing smaller size nanoparticles of size 23.2 nm and 4.7 nm.
Figure 4:
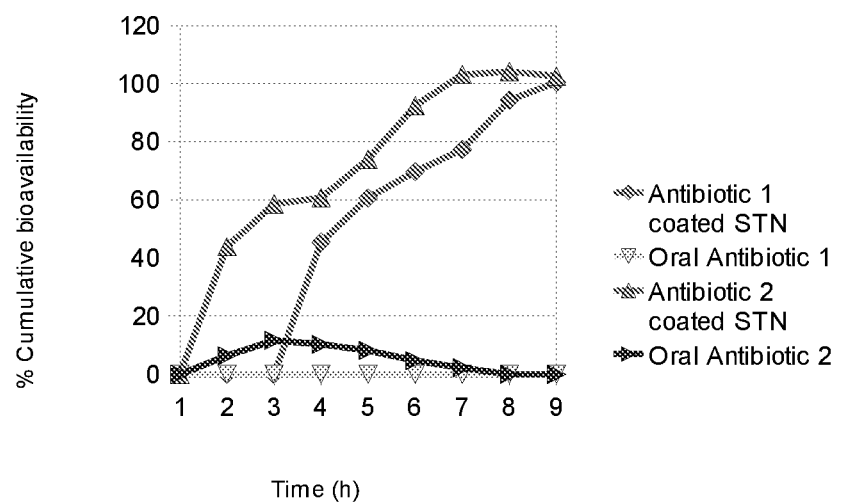
FIG. 4: Percentage cumulative bioavailability vs time profile of two antibiotics from coated STN indicating that ceftriaxone as antibiotic 1 and sulbactam as antibiotic 2 have >100% at 7 hr after STN oral delivery where as the oral delivery of normal drugs is zero.
Figure 5:
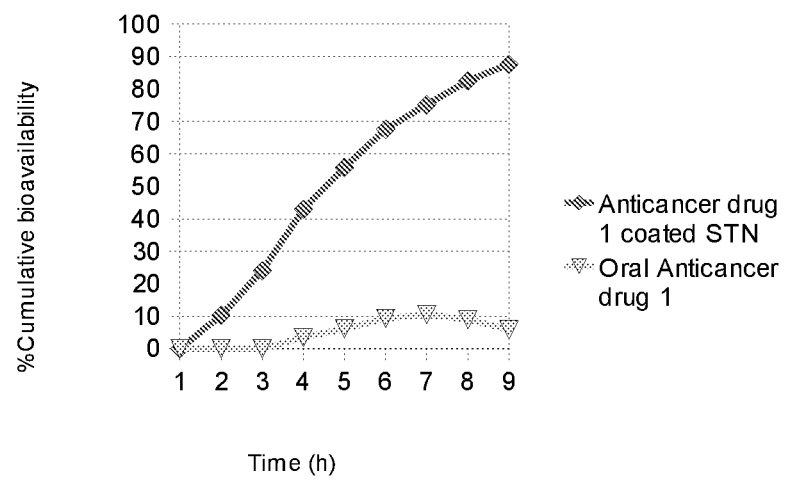
FIG. 5: Percentage Bioavailability vs time profile of anticancer drug (docetaxel) from coated STN indicating >90% release after 9 hr against conventional oral form with <10% bioavailability
Figure 6:
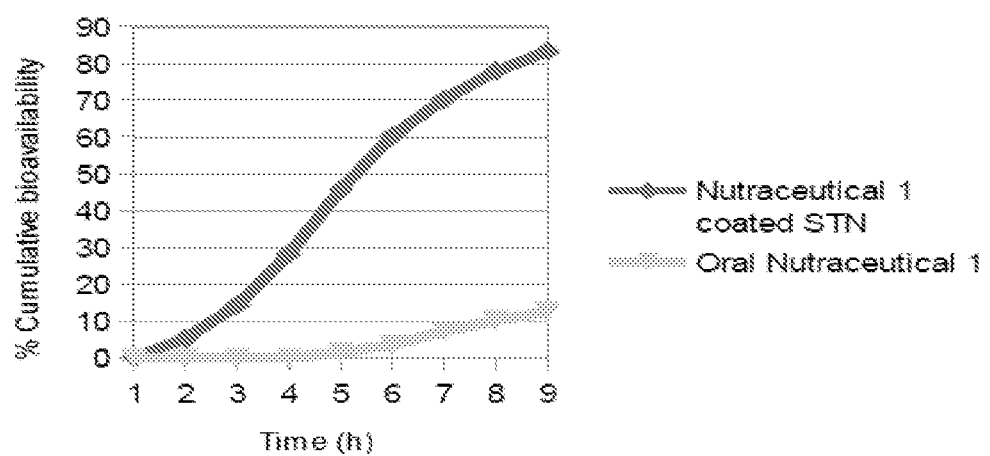
FIG. 6: Percentage Bioavailability vs time profile of Nutraceutical 1 (Coenzyme Q 10) from coated STN indicating >80% bioavailability at 6 hrs in comparison to conventional formulations with <15% bioavailability
Figure 7:
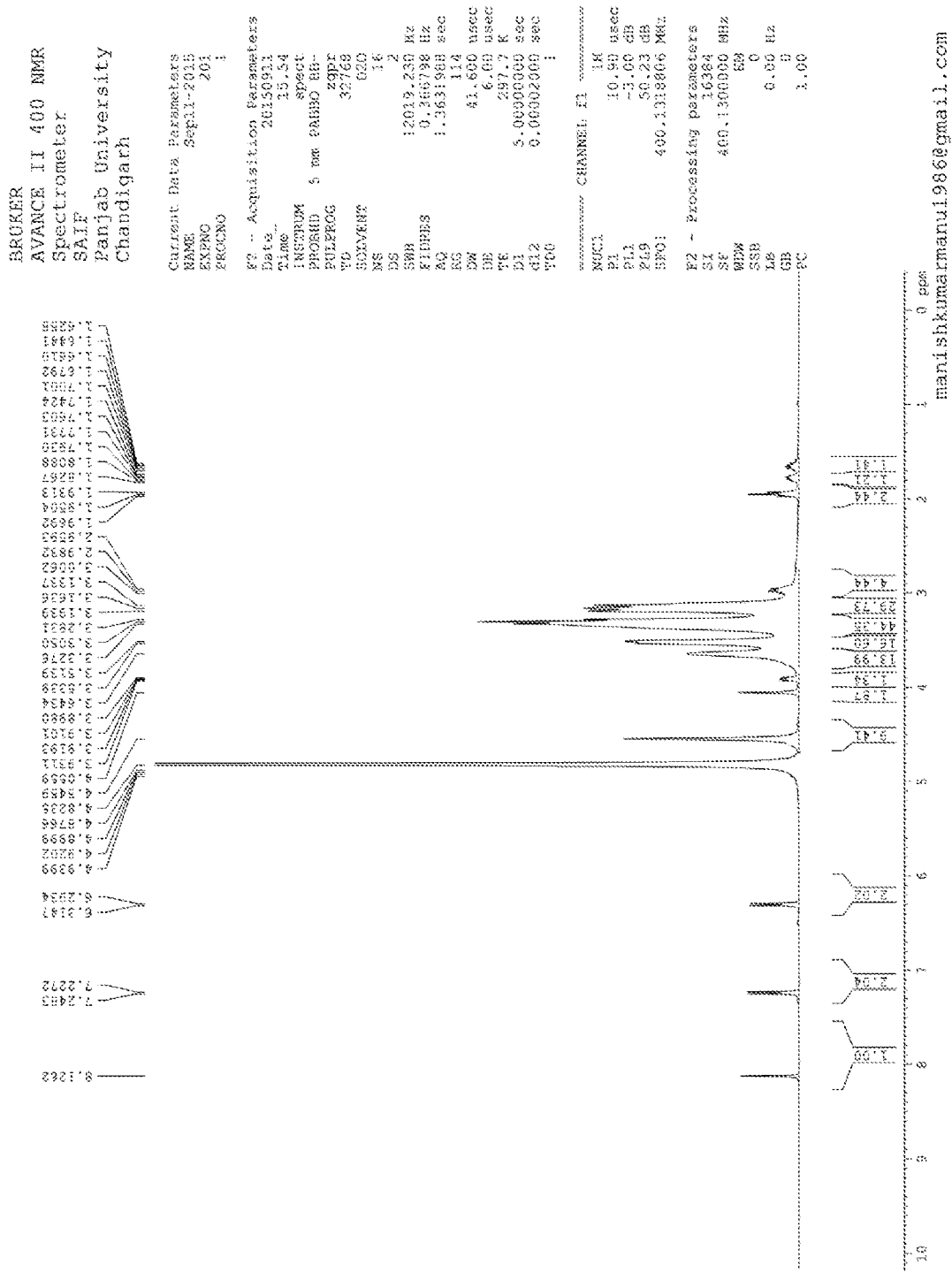
FIG. 7: PEG-DEXTRAN-FOLIC ACID NMR Spectra: PEG-DEXTRAN semi interpenetrating network (physical blend/mixture) with folic acid appended through surface blooming shows individual peaks characteric similar to NMR of individual component and doesn't show any additional peak or decrease in peak intensity indicating that there is no chemical covalent bond formation and no chemical conjugation occur.

Folic acid: Typical aliphatic proton peaks (3 Peaks) at 1.62 to 1.96 ppm. 3.9, 4.05 and 4.55 ppm (typical peaks of folic acid.) It also shows characteristic peaks of folic acid at 6.31 ppm (m, Ar, 2H), 7.25 PPM (m, Ar, 2H), and 8.12 ppm (s, $NH_2$).

PEG: Typical proton peak of PEG at 3.28 to 3.32 ppm attributed to methylene proton peak of methylene group ($—CH_2$) of PEG.

Dextran: Typical proton peak of dextran between 3 to 4 ppm (9H, m) and at 4.82 ppm (1H, s, H) from ring of dextran.

DETAILED DESCRIPTION OF THE INVENTION

The embodiments herein and the various features and advantageous details thereof are explained more fully with reference to the non-limiting embodiments that are illustrated in the accompanying figures & tables and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Definitions

As used herein "Stealth Targeted Nanoparticles" (STN) means nanoparticles loaded with therapeutic agent (by means of physical entrapment), in ligand appended, non lipidic polymeric matrix for targeted delivery of poorly bioavailable therapeutic agents with an increase in bioavailability to 70-90%.

As used herein "Poorly bioavailable therapeutic agents" (PBTAs) means small molecule therapeutic agents including but not limited to BCS class III/IV drugs or nutraceuticals or any other agent having poor permeability and challenge of bio-availability in body which are used to provide therapeutic effect for cancer, bacterial/fungal infections, arthritis, pain, viral infections, age related diseases, contagious diseases, orphan diseases, hereditary diseases, life style diseases, deficiency diseases, immune disorders and other nutritional support requirements by delivering said small molecule allopathic, herbal, natural therapeutic agents in condition of need.

The current invention relates to a technology for oral delivery of Poorly Bio-available Therapeutic Agents (PBTA) and the formulations derived using that technology. Poorly Bio-available Therapeutic Agents may belong to BCS class III/IV drugs or nutraceuticals or any other agent which is required to be orally delivered having challenge of bio-availability in body, together termed as therapeutic agent.

In one embodiment of the invention, targeted delivery of poorly bio-available agents (BCS class III and BCS class IV drugs/nutraceuticals) is described for oral delivery and for the benefit of or treatment of related conditions.

In yet another embodiment the targeted delivery is through nanoparticles. Conventionally nanoparticles have a tendency to be phagocytosed by opsonins/macrophages, thus making them poorly bio-available. Another embodiment of current invention where the problem of phagocytosis is overcome using stealth polymers.

In one aspect the present invention relates to stealth targeted nanoparticle (STN) technology designed for oral delivery of Poorly Bio-available Therapeutic Agents (PB-TAs), herein after termed as PBTA/PBTAs, and formulations made thereof.

In yet another aspect of invention Stealth targeted nanoparticles (STN) are pH sensitive.

The kinetics of drug release from nanoparticles depends on the strength of hydrophobic interactions between the polymer and drug and polymer degradation rate. The uptake and distribution of nanoparticles depend on its size. Nanoparticles of size ~20 nm are utilized for extended circulation, while ~100 and ~200 nm particles are utilized for passive targeting and intracellular drug delivery respectively. Though nanoparticles have many advantages over other conventional drug delivery systems certain properties like surface hydrophobicity and surface charge needs to be altered so as to increase the uptake of nanoparticles into cells. This is being done by manipulating the use of polymers. Coating the nanoparticles with chitosan which is positively charged significantly enhances the uptake and modulates the drug efflux of anticancer agents as has been reported in prior arts.

Disadvantages of nanoparticles reported in prior arts are:
a) Involves complicated processes that leads to higher manufacturing costs which may in turn lead to increase in the cost of formulation; b) Involves use of harsh, toxic solvents in the preparation process; c) May trigger immune response and allergic reactions; d) Extensive use of poly (vinyl alcohol) as stabilizer may have toxicity issues; e) use of lipids to entrap drug; f) formation of covalent bonds between therapeutic agent and polymer.

Hence, Stealth Targeted Nanoparticle (STN) technology was invented to overcome the shortcomings of prior arts. The small molecule therapeutic agents with poor bioavailability are delivered to the target site using non protein target agent and bioavailability is significantly enhanced.

In still another aspect of current invention the stealth targeted nanoparticles are made of biocompatible polymers.

In another aspect of current invention the stealth polymers evade clearance from the body and remain in circulation for a longer period of time allowing longer circulation in blood stream and more penetration into tissues over an extended period of time.

Surface opsonisation promotes the removal of particles from the circulation within seconds to minutes through the mononuclear phagocytic system (MPS), reticuloendothelial system (RES), by Kupffer cells, phagocytic macrophages permanently located in the liver. In the bloodstream, opsonins interact with nanoparticles by van der Waals, electrostatic, ionic, and hydrophobic/hydrophilic forces. Therefore, the surface features of the nanocarriers have a key role in the opsonisation process. Hydrophobic and charged particles undergo higher opsonisation as compared to hydrophilic and neutrally charged particles. Therefore, the biodegradable polymer used for stealth technology is preferably hydrophilic. The said biodegradable polymer is a mixture of stealth biocompatible polymer and a polysaccharide. Either natural and/or semisynthetic polysaccharides and/or synthetic polymers can be used for this purpose. Dextran (Dex), polysialic acid (PSA), hyaluronic acid (HA), chitosan (CH), and heparin are the natural polysaccharides. Synthetic polymers include polyvinyl pyrrolidone (PVP), polyvinyl alcohol (PVA), polyacrylamide (Pam), poly(ethylene glycol) (PEG), and PEG-based copolymers such as poloxamers, poloxamines, and polysorbates.

Stealth polymers are selected from a group consisting of polyvinyl pyrrolidone (PVP), polyvinyl alcohol (PVA), polyacrylamide (Pam), poly(ethylene glycol) (PEG) and PEG-based copolymers such as poloxamers, poloxamines, polysorbates, PEG derivatives, PEG-2000 to 20000, monomethoxy PEG-2000 to 20000, monomethoxy PEG methyl ether, d-PEG, biotinylated-PEG, Hydrophilic poly (oxazoline) (PMOXA), poly(2-ethyl-2-oxazoline), poly(hydroxyethyl-asparagine) (PHEA), N-(2-hydroxypropyl) methacrylamide (HPMA), poly(sulfobetaine), poly(carboxybetaine), hyperbranched polyglycerol, poly(hydroxymethylethylene hydroxymethylformal), PEG-succinimidyl-succinate, NHS-monomethoxy PEG butanoic acid, NHS-monomethoxy PEG butanoic acid-lysine, monomethoxy PEG aldehyde (MW 20000 Da), PEG p-nitrophenyl carbonate ester, 20 kDa linear monomethoxy-PEG aldehyde and the like. Of these PEG alone or in its derivative form is the best representative of the polymers used to produce stealth effect. This neutral, flexible, and hydrophilic material can in fact properly produce surface barrier layers that reduce the adhesion of opsonins present in the blood serum on the nanoparticles making them "invisible" to phagocytic cells. According to their hydrophilic and flexible nature, the PEG chains can acquire an extended conformation on particle surface. Opsonins attracted to the particle surface compress the extended PEG chains that shift to a more condensed and higher energy conformation. As a consequence, the repulsive forces counterbalance the attractive forces between opsonins and the particle surface.

In yet another aspect of current invention the STN technology comprises of a polymeric back bone of a mono and or polysaccharide agent along with stealth polymer. This polysaccharide agent is selected from group comprising guar gum, gum arabic, gum tragacanth, larch gum, gum karaya, locust bean gum, agar, alginates, carageenan, pectins, tragacanth gum, starch, c-starch, xanthan gum, succinoglucan, pullulan chitin, chitosan, polysialic acid, hyaluronic acid, heparin, starch/acrylic acid graft copolymer, complex carbohydrates dextran and the like.

According to another embodiment of the invention, polymer and polysaccharide agent (polymeric backbone) together form a semi inter penetrating network without covalent bonding which is termed as polymeric matrix.

According to yet another embodiment, polymeric matrix is water soluble and hence has more biocompatibility than lipid based matrices.

According to the said embodiment STN comprise of a nonlipidic polymer matrix, comprising of at least one stealth polymer and at least one poly-saccharide. The said polymeric matrix is non lipidic in nature and does not involve covalent bond or conjugation. STN further comprise of a non protein target agent/ligand and one or more than one poorly bioavailable therapeutic agent which are physically entrapped inside the non lipidic polymer matrix without conjugation or covalent bond.

Selection of appropriate grade of stealth polymer is essential for strong polymeric matrix without which the semi inter penetrating network formed will be loose and may not result in formulation.

According to the said embodiment to achieve a good strength of polymeric matrix choice of grade of polymer, polysaccharide and their ratio is very critical.

According to another embodiment herein, the stealth targeted nanoparticles are targeted wherein the targeting agent/ligand is a non protein agent. This non protein targeting entity/agent/ligand is selected from a group consisting of small molecule such as a neurotransmitter, hormone, a pharmaceutical drug, vitamin, anti oxidants, toxin, or parts of the outside of a virus or microbe such as but not limited to glucose-6-phosphate, mannose, palmitate, myristate, geranylgeraniol, farnesol, dolichol, cholesterol, ubiquinone (coenzyme Q 10), folic acid, biotin, cyanocobalamine, hydoxycobalamine, sterol, bile acids, squalene, wheat germ aglutinin, pyridoxal, phosphate, tocopherol, lipidic growth factor, glucosamine, glycosamine, glycolipids and the like.

According to yet another embodiment the target agent is vitamin, preferably folic acid, wherein this targeting ligand facilitates cellular targeting which binds to specific cell surface receptors, enabling the nanoparticles to preferentially accumulate at their intended site of action across gastro intestinal lumen.

According to yet another embodiment, the said targeting agent/ligand is physically entrapped in semi inter penetrating network of one or more polymer along with polysaccharide and is not covalently linked.

According to yet another embodiment, the said targeting agent does not require covalent binding or chemical reaction or conjugation to occur. Further, the said targeting agent does not require any chemical cross linking agent or any activation agent to bind to polymer matrix or to therapeutic agent. The said targeting agent is physically trapped inside polymer matrix using heat as cross linking agent. Alternatively, vacuum evaporation or sublimation may also be used for ligand appending with polymer matrix.

The said targeting agent/ligand is polar and is physically entrapped inside polymer matrix and moves to surface due to blooming which allows binding to receptors.

According to yet another preferred embodiment of current invention the targeting agent is vitamin in a range of about 0.01 mg to 10 mg of formulation composition of STN.

According to yet another preferred embodiment of current invention the targeting agent is folic acid in a range of about 0.01 mg to 10 mg of formulation composition of STN.

According to another embodiment of current invention, stealth targeted nanoparticles (STN) are formed using water soluble polymer matrix which is physically cross linked with heat to trap targeting agent and therapeutic agent of one or more of Poorly Bio-available Therapeutic Agents (PBTAs). The composition of STN when administered, form smaller nanoparticles of size ≤20 nm which increase bioavailability of said PBTA to >70%, preferably 70-90% and is administered orally in the subjects of need.

The stealth targeted nanoparticles of Poorly Bio-available Therapeutic Agent (PBTA) where a PBTA may be a drug (BCS class III and BCS class IV)/nutraceuticals, diagnostic agent, sa salt or an isomer or a derivative thereof or a mixture thereof. PBTA described herein, mostly involves non peptide, non biological, small molecule agents which include drugs like antibiotics, antivirals, anti osteoporosis, anti arrhythmic, ACE inhibitors, antihistamines, anticancer, anti fungal, diuretic, anthelmintic, anti-tubercular, anti-rheumatoid, anti-ulcer, immunosuppressant and other molecules with established therapeutic effects against one or other disease and mixture thereof. These PBTAs are highly polar and ionized molecule, i.e. BCS class III and IV drugs wherein the partition co-efficient of them falls in negative value range thereby making such drug less effective in oral route. In the oral route, often the bio-availability of these PBTAs, in particular antibiotics and some anticancer drugs are as low as <1%. Furthermore, degradation of these drugs occurs at acidic pH of stomach, before the molecule could reach the small intestine for absorption. Accordingly, inter alia, there were challenges to formulate such PBTAs, antibiotics in an oral formulation, preserving therapeutic value and then design a predefined bio-availability at targeted site in a required therapeutic range.

According to another embodiment of the invention the said poorly bio-available therapeutic agents PBTAs which may be drugs (BCS class III and BCS class IV)/nutraceuticals or any other poorly bio-available entity/agent and their combination thereof comprise the therapeutic agents of the stealth targeted nanoparticles formulations. The said therapeutic agents are selected from a group comprising of antibiotics, antivirals, anti osteoporosis, anti arrhythmic, ACE inhibitors, antihistamines, anticancer, anti fungal, diuretic, anthelmintic, anti-tubercular, anti-ulcer, anti-rheumatoid drugs, immunosuppressant and other molecules with established therapeutic effects against one or other disease and nutraceuticals and have poor bioavailability.

In a preferred embodiment, the PBTAs are drugs and co drugs selected from a class of antibiotics such but not limited to beta-lactam antibiotics such as, cephalosporins, carbapenems, cephamycin, monobactams and penicillins alone or in a combination with beta-lactamase inhibitor, polymixin, sulphonamides, tetracyclines, aminoglycosides, lincosamides, streptogramins, ketolides, glycylcyclines, phenicols, oxazolidinones, ansamycins, glycopeptide, lipopeptides, cyclic lipopeptides, fluoroquinolones, fosfomycins, oxalidinones, imidazole, macrolides, anti metabolites, furanes etc or pharmaceutically acceptable salts, isomers and derivative thereof.

The term antibiotic is defined as a agent having therapeutic effect to kill bacterial growth or to stop bacterial growth.

In another preferred embodiment the said therapeutic agent is antibiotic drug.

In another preferred embodiment the said therapeutic agent is combination of one or more antibiotic drugs delivered orally using STN technology.

In yet another preferred embodiment the said therapeutic agent is a combination of drugs. The combination of drugs is selected from groups of antibiotics but not limited to ceftriaxone, cefepime, ceftazidime, cefuroxime, cefexime, cefpodoxime, cefaclor, cefoperazone, cefadroxil, ceftibuten, cefdinir, cefditoren, ceftizoxime, cefamandole, cefazoline, cefonicid, cefoxitin, cefprozil, cephalexin, cephapirin, ceftobiprole, ceftolozane, ceftaroline, cephradine, meropenem, doripenem, eratpenem, panipenem, tebipenem, sanfetrinem, tomopenem, biapenem along with amikacin, etimicin, gentamicin, tobramycin, polymixin, colistin, vancomycin, teicoplanin, dalbavancin, oritavancin, telavancin, azithromycin, erythromycin, roxithromycin, clindamycin, lincomycin dicloxacillin, ampicillin, clarithromycin, amoxicillin, sulbactam, tazobactam, clavulanic acid, avibactam, relebactam, RPX709, NXL104, AVE1330A and the like or pharmaceutically acceptable salts, isomers, derivative and mixtures thereof.

In yet another preferred embodiment the one of the therapeutic antibiotic agent is a beta lactam antibiotic along with one or more of co-drug beta lactamase inhibitors. The said beta-lactam drug is selected from a group of ceftriaxone, cefepime, ceftazidime, cefuroxime, cefexime, cefpodoxime, cefaclor, cefoperazone, cefadroxil, ceftibuten, cefdinir, cefditoren, ceftizoxime, cefamandole, cefazoline, cefonicid, cefoxitin, cefprozil, cephalexin, cephapirin, ceftobiprole, ceftolozane, ceftaroline, cephradine or a pharmaceutically acceptable salt thereof and the said co-drug is beta-lactamase inhibitor selected from sulbactam/tazobactam/clavulanic acid/avibactam, relebactam, RPX709, NXL104, AVE1330A or pharmaceutically acceptable salts, isomers, derivative and/or mixtures thereof.

In certain aspect of current invention one of the therapeutic antibiotic agent is a carbapenem antibiotic along with one or more of co-drug beta lactamase inhibitors. The said carbapenem drug is selected from a group of meropenem, doripenem, eratpenem, panipenem, tebipenem, sanfetrinem, tomopenem, biapenem or a pharmaceutically acceptable salt thereof and the said co-drug is beta-lactamase inhibitor selected from sulbactam/tazobactam/clavulanic acid/avibactam, relebactam, RPX709, NXL104, AVE1330A or pharmaceutically acceptable salts, isomers and derivative thereof.

In another aspect of current invention one of the therapeutic antibiotic agent is a carbapenem antibiotic along with one or more of second antibiotic drug whose mechanism of killing bacteria is different from that of carbapenems. The said carbapenem drug is selected from a group of meropenem, doripenem, eratpenem, panipenem, tebipenem, sanfetrinem, tomopenem, biapenem or a pharmaceutically acceptable salt thereof and the said second antibiotic is one or more of drug or pro drug of aminoglycoside, glycopeptide, lipopeptide, polymixin, quinolones, imidazoles or pharmaceutically acceptable salts, isomers and/or derivative.

In another aspect of current invention one of the therapeutic antibiotic agent is a cephalosporin antibiotic along with one or more of second antibiotic drug whose mechanism of killing bacteria is different from that of cephalosporins. The said cephalosporin drug is ceftriaxone, cefepime, ceftazidime, cefuroxime, cefexime, cefpodoxime, cefaclor, cefoperazone, cefadroxil, ceftibuten, cefdinir, cefditoren, ceftizoxime, cefamandole, cefazoline, cefonicid, cefoxitin, cefprozil, cephalexin, cephapirin, ceftobiprole, ceftolozane, ceftaroline, cephradine or a pharmaceutically acceptable salt thereof and the said second antibiotic is one or more of drug or pro drug of aminoglycoside, glycopeptide, lipopeptide, polymixin, quinolones, imidazoles or pharmaceutically acceptable salts, isomers and/or derivative.

In another embodiment, therapeutic agents are selected from a class of anticancer drugs comprises but not limited to anti-metabolites masquerade as purines, alkyl agents such as cisplatin, carboplatin, oxaliplatin, mechlorethamine, cyclophosphamide, chlorambucil, ifosfamide, plant alkaloids including vinca alkaloids such as vincristine, vinblastine, vinorelbine, vindesine, podophyllotoxins: etoposide and teniposide, taxanes such as docetaxel, paclitaxel, topoisomerase inhibitos such as irinotecan and topotecan, cytotoxic antibiotics such as actinomycin, anthracyclines, doxorubicin, dactinomycin, cytarabine, bortezomib, gemcitabine, daunorubicin, valrubicin, idarubicin, epirubicin, bleomycin, fludarabine, clatribine, Methotrexate, 5-fluro uracil, amscrine, cladribine, carmustine plicamycin, mitomycin, pemetrexate, capecitabine, dasatinib, erlotinib, fludarabine, imatinib, lapatinib, nilotinib, sorafenib, sunitinib, thalidomide, 9-nitrocamptothecin, curcumin, exemestane, mitotane, raloxifene, emodin, methotrexate, tamoxifen, benzyl isothiocyanate, melphalan, meso-tetraphenyl porphine, α-mangostin, quercetin, epigallocatechin gallate, 10-hydroxycamptothecin, thymopentin, rapamycin, altretamine, anagrelide, anastrazole, bexarotene, bicalutamide, finasteride, gefitinib, hydroxycarbamide, ibandronic acid, imatinib, lapatinib, lenalidomide, letrozole, mercaptopurine, nilutamide, procarbazine, raloxifene, rubitecan, sobuzoxane, sunitinib, tamibarotene, tamoxifen, temozolomide, thalidomide, thioguanine, toremifene, treosulfan, vorinostat and any other agent used for cancer management with known poor bioavailability or pharmaceutically acceptable salts, isomers and derivative.

In another embodiment, therapeutic agents are selected from a class of Immunosuppressant drugs comprises but not limited to azathioprine, cyclosporine, daclizumab, mycophenolate mofetil, prednisone, sirolimus, tacrolimus, everolimus, basiliximab muromonab CD3 and any other agent used with known poor bioavailability or pharmceutically acceptable salts, isomers and derivative. The said therapeutic agents may be used alone or in combination with other therapeutic agents.

In an another embodiment, therapeutic agents are selected from a class of anti inflammatory drugs comprises but not limited to celecoxib, diclofenac, diflunisal, etodolac fenoprofen, flurbiprofen, ibuprofen, indomethacin, ketoprofen, ketorolac, meloxicam, nabumetone, naproxen, oxaprozin, piroxicam, salsalate, sulindac, tolmetin and the like and any other agent used with known poor bioavailability or pharmceutically acceptable salts, isomers and derivative.

According to the said embodiments the said therapeutic agent are of natural or synthetic origin or of herbal origin.

In another embodiment, the said therapeutic agents are selected from a group of poorly permeable/bioavailable nutraceuticals comprises but not limited to vitamins, antioxidants, dietary minerals, essential elements, proteins, herbal extracts, herbal supplement and the like and any other agent used with known poor bioavailability of synthetic or natural origin.

According to yet another embodiment of current invention STN is used for enhanced bioavailability by oral delivery of PBTA along with one or more easily bioavailable therapeutic agent in subject of need.

In yet another embodiment of current invention, stealth targeted nanoparticle technology for oral delivery of PBTAs and the formulations made thereof provide protection of drug and body from unwanted deposition, which could lead to unwanted reactions and metabolism and hence reduce side effects and adverse effects drastically.

In yet another embodiment of current invention, stealth targeted nanoparticle technology for oral delivery of PBTAs and the formulations made thereof provide ccontrolled rate and modality of delivery to pharmacological receptor wherein the target agent/entity/ligand is a non protein target for the optimum delivery of said therapeutic agent to deliver PBTAs across gastro intestinal lumen.

According to another embodiment of current invention, stealth targeted nanoparticle technology for oral delivery of PBTAs and the formulations made thereof can deliver large amounts of said therapeutic agent to the body and mitigate the challenge of delivering large doses of therapeutic agent, especially as required in antibiotics, immunosuppressants and anti cancer drugs and some nutraceuticals.

In yet another embodiment STN technology may further comprises of surface modifiers, protective colloids, cryoprotectants, stabilizers that prevent aggregation and/or Ostwald ripening of the nanoparticles during and after processing. Surface modifiers are chosen from the list of pharmaceutically-acceptable substances and typically possess surface active properties capable of wetting the large drug crystals and providing steric and/or ionic stabilization to the resulting nanometer-size drug particles. Some of the most commonly-used stabilizers include povidones, phospholipids, polysorbates, poloxamers, cellulosics, and anionic surfactants.

According to yet another embodiment, STN technology may further comprise of certain adjuvants or excipients known to a person skilled in art and well established in industry such as but not limiting to amino acids, chelating agents, common salts of sodium, potassium, magnesium, zinc, selenium and the like.

According to another aspect of current invention the entrapment efficiency of the said therapeutic agent is achieved best when the weight ratio of stealth polymer to polysaccharide forming polymeric backbone is 1:10:10:1, more specifically 1:5 to 5:1 and still more preferably polymer to polysaccharide:1:5.

According to the said embodiment this ratio is critical to make it stable semi interpenetrating network which allows adsorption, physical cross linking and is a green chemistry approach.

Accordingly, the entrapment efficiency is decreased due to loosening of structure and the particle size will be affected. The ratio is critical to the technology because it also affects the integrity of the system and does not allow it to be semi interpenetrating network leading to failure to form nanoparticles.

As per preferred embodiment the technology stealth targeted nanoparticle (STN) comprise essentially of a stealth polymer PEG or a derivative thereof to form polymeric matrix along with a polysaccharide agent (polymeric backbone) dextran in the ratio of 1:10 to 10:1, wherein both form a semi interpenetrating network and are physically cross linked, without covalent bonding or conjugation.

According to yet another preferred embodiment the stealth polymer is preferably poly ethylene glycol in the range from 2 kDa to 20 kDa.

According to one embodiment PEG is preferably 20 kDa.

According to still another preferred embodiment the polymeric backbone is polysaccharide, preferably dextran in the range of 3 to 2000 kDa.

According to one embodiment Dextran is between 40 kDa to 70 kDa. Dextran higher than 40 kDa has poor renal clearance and cause kidney problems and hence dextran of ≤40 kDa is used in current invention.

According to the said embodiment, dextran in current invention is used to provide burst effect by swelling in aqueous medium which breaks nanoparticles into further smaller nanoparticles at a particular pH during intestinal delivery.

According to a preferred embodiment of current invention stealth targeted nanoparticles and compositions made thereof involve active targeting by means of a non protein target ligand such as folic acid. Conventionally, active targeting is achieved using affinity ligands such as proteins, peptides, antibodies and aptamers by means of conjugation or covalent bonding. The current invention has disclosed use of non protein target agent which is preferably folic acid for gastro intestinal delivery across lumen. The other targeting agents which can be used include oligosaccharides (carbohydrates), viral proteins, fusogenic residues, molecules of endogenous origin, blood carbohydrate (lectin) receptors, Fc receptors, complement receptors, interleukin receptors, lipoprotein receptors, transferin receptors, scavenger receptors, receptors/epitopes expressed on tumor cells, and cell adhesion receptors.

According to a preferred embodiment of current invention stealth targeted nanoparticles and compositions made thereof contains stealth polymer as PEG, preferably PEG 20,000; polysaccharide as dextran, preferably dextran 40 kDa; target ligand as a vitamin in range of 0.01 mg to 10 mg and is preferably folic acid; therapeutic agent as poorly bioavailable drug/nutraceutical; further the weight ratio of PEG to Dextran is in the range of 1:10 to 10:1, more preferably 1:5 to 5:1 and ligand and the therapeutic agent are physically entrapped in polymer matrix, without conjugation/covalent bond to form stable stealth targeted nanoparticles of size ≤1000 nm. The nanoparticles swell and burst after oral administration to form smaller nanoparticles of size ≤20 nm to improve cumulative bioavailability to >100% of said therapeutic agent. The ratio of said PBTA to ligand appended polymer matrix is 1:1 to 1:10, preferably 1:4.

According to yet another preferred embodiment of STN the composition and method of preparation wherein the said stealth polymer is PEG 20,000 (20 kDa); the said polysaccharide is dextran, 40 kDa; the target ligand is a folic acid in range of 0.01 mg to 10 mg; the said therapeutic agent is ceftriaxone along with sulbactam and adjuvant disodium EDTA, the weight ratio of PEG to Dextran is 1:5 to physically entrap the constituents and the ratio of said poorly bioavailable therapeutic agent to said ligand appended polymer matrix is 1:4 to form stable, stealth targeted nanoparticles of size ≤1000 nm by process of spray drying. These nanoparticles swell and burst after oral administration to form smaller nanoparticles of size ≤20 nm to improve cumulative bioavailability to >100% of said therapeutic agent/s. These STNs are coating, filled in sachet and are administered orally in subjects of need to cater drug resistant bacterial infections.

According to yet another embodiment of current invention a method of preparation of a composition for targeted delivery of PBTA comprising of stealth targeted nanoparticles, comprising following steps:

a) preparing a semi-inter-penetrating-network of a stealth polymer, a polysaccharide and a targeting ligand by dissolving polymer and polysaccharide in a fixed weight ratio with targeting ligand in aqueous solution;
b) adding the said poorly bioavailable therapeutic agent or a mixture of agents to above semi inter penetrating network and mixing under inert atmosphere, for a few minutes to form a clear solution;
c) heating solution of above stage b between 120 to 170 degree celcius to harden the polymer matrix during spray drying to obtain stealth targeted nanoparticles of size ≤1000 nm.

According to a preferred embodiment of current invention the method of preparation of composition for targeted delivery of poorly bioavailable therapeutic agent comprising of stealth targeted nanoparticles contains stealth polymer as PEG 2-20 kDa and polysaccharide as Dextran ≤40 kDa, further the weight ratio of polymer to polysaccharide is 1:10 to 10:1, more specifically 1:5. The targeting ligand is a vitamin, preferably folic acid in range of 0.01 mg to 10 mg of the formulation composition and the polysaccharide and ligand are physically entrapped in semi interpenetrating network without covalent bonding or conjugation to form ligand appended non lipidic polymeric matrix. Further, the PBTA or mixture of agents are of synthetic or natural origin and are physically entrapped in ligand appended non lipidic polymer matrix to form STN by spray drying process. The ratio of said PBTA to ligand appended polymer matrix is 1:1 to 1:10, preferably 1:4. More specifically the targeting ligand is physically entrapped without covalent bonding by heat cross linking and ligand is polar and moves to surface by blooming effect. The ligand appended therapeutic agent loaded non lipidic polymer matrix formed as result of spray drying further swells and bursts after oral administration to produce smaller nanoparticles of size ≤20 nm. Such STN are administered orally to provide desired therapeutic effects in condition of need.

According to another preferred embodiment of current invention the method of preparation of composition for targeted delivery of PBTA further optionally comprise of formulating the nanoparticles in multi unit particulate system (MUPS)/granules and optionally enteric coating the said MUPS/granules processed as tablet, capsules, sachet and any other acceptable oral form.

Following are some of the non-limiting illustrative examples for the embodiments of the invention:

Example 1

Dissolve 1:1 ratio of Dextran 40 kDa, PEG-20 kDa and folic acid (FA) in around ¾$^{th}$ quantity of 0.1% NaOH solution in water under continuous stirring. Dissolve docetaxel in 1:1 of tween 80:ethanol solution. Add this mixture to the previously dissolved FA-PEG-DEXTRAN solution. Sonicate, if required. The formulation is spray dried with inlet temperature of 140 degree celcius to get fine nanoparticles in powder form.

Example 2

Dissolve 2:1 ratio of Dextran 30 kDa, PEG-20 kDa and biotin in around ¾$^{th}$ quantity of water under continuous inert stirring atmosphere. Dissolve paclitaxel in 1:1 of tween 80:ethanol solution. Add this mixture to the previously dissolved FA-PEG-DEXTRAN solution. Sonicate if required. The formulation is spray dried with inlet temperature of 130 degree celcius to get fine nano particles in powder form.

Example 3

Dissolve 1:1 ratio of Chitosan, PEG-4000 and hydroxycobalamine in around ¾$^{th}$ quantity of 0.1% acetic acid solution under silverson homogenizer till complete dispersion. Dissolve zolendronic acid in sodium citrate solution. Add this mixture to the previously dissolved FA-PEG-CHITOSAN solution. Sonicate till complete dissolution. The formulation is spray dried with inlet temperature of 145 degree celcius to get fine nanoparticles in powder form. The particles may be enteric coated with suitable polymer.

Example 4

Dissolve 1:3 ratio of Dextran 40 kDa, PEG-20 kDa and n-acetyl cystein (NAC) in around ¾$^{th}$ quantity of water under continuous stirring and inert atmosphere. Dissolve pemetrexed disodium in water. Add this mixture to the previously dissolved NAC-PEG-DEXTRAN solution for a few minutes. The formulation is spray dried with inlet temperature of 140 degree celcius to get fine nanoparticles in powder form.

Example 5

Dissolve 1:4 ratio of Dextran 40 kDa, PEG-20 kDa and n-acetyl cystein (NAC) in around ¾$^{th}$ quantity of 0.1% NaOH solution in water in a beaker under continuous stirring. Dissolve bortezomib in tertiary butyl alcohol. Add this mixture to the previously dissolved NAC-PEG-DEXTRAN solution. Sonicate till complete dissolution. The formulation is spray dried with inlet temperature of 120 degree celcius to get fine nanoparticles in powder form.

Example 6

Dissolve 1:1 ratio of Dextran 40 kDa, PEG-20 kDa and folic acid (FA) in around ¾$^{th}$ quantity of 0.1% NaOH solution in water under continuous stirring. Dissolve 2:1 ceftriaxone sulbactam in water. Add disodium EDTA. Add this mixture to the previously dissolved FA-PEG-DEXTRAN solution. The formulation is spray dried with inlet temperature of 140 degree celcius to get fine nanoparticles in powder form. The particles may be enteric coated with suitable polymer.

Example 7

Dissolve 8:1 ratio of Dextran 40 kDa, PEG-20 kDa and folic acid (FA) in around ¾$^{th}$ quantity of 0.1% NaOH solution in water under continuous stirring under inert atmosphere. Dissolve meropenem and avibactam in water. Add this mixture to the previously dissolved FA-PEG-DEXTRAN solution. The formulation is spray dried with inlet temperature of 140 degree celcius to get fine nanoparticles in powder form.

Example 8

Dissolve 2:1 ratio of Dextran 40 kDa, PEG-20000 and biotin in around ¾$^{th}$ quantity of water under continuous stirring. Dissolve 2:1 ratio of cefepime-vancomycin in water. Add 1-arginine dissolved in water. Add this mixture to the previously dissolved BIOTIN-PEG-DEXTRAN solution. The formulation is spray dried with inlet temperature of 140 degree celcius to get fine nanoparticles in powder form.

Example 9

Dissolve 1:2 ratio of Dextran 40 kDa, PEG-20 kDa and folic acid in around ¾$^{th}$ quantity of 0.1% NaOH solution in water in a beaker under continuous stirring. Dissolve 2:1 ratio of ceftriaxone-vancomycin in water. Add 1-arginine and disodium EDTA. Add this mixture to the previously dissolved FA-PEG-DEXTRAN solution. The formulation is spray dried to get fine nanoparticles in powder form. The particles may be enteric coated with suitable polymer.

Example 10

Dissolve 7:1 ratio of Chitosan, PEG-2000 and biotin in around ¾$^{th}$ quantity of water under homogenizer till complete dispersion. Dissolve 2:1 cefepime sulbactam in water. Add this mixture to the previously dissolved BIOTIN-PEG-CHITOSAN solution. Sonicate till complete dissolution. The formulation is spray dried with inlet temperature of 150 degree celcius to get fine nano particles in powder form. The particles may be enteric coated with suitable polymer.

Example 11

Dissolve 9:1 ratio of Dextran 30 kDa, PEG-20 kDa and folic acid (FA) in around ¾$^{th}$ quantity of 0.1% NaOH solution in water under stirring for a few minutes till complete dissolution. Dissolve meropenem and etimicin in water. Add sodium carbonate and disodium EDTA. Add this mixture to the previously dissolved FA-PEG-DEXTRAN solution. The formulation is spray dried with inlet temperature of 170 degree celcius to get fine nanoparticles in powder form.

Example 12

Dissolve 9:1 ratio of Chitosan, PEG-2000 and n-acetyl cystein (NAC) in around ¾$^{th}$ quantity of water under stirring for a few minutes inert atmosphere till complete dissolution. Dissolve 8:1 ratio of ceftazidime tobramycin in water. Add glucose 6 phosphate and 1-arginine. Add this mixture to the previously dissolved FA-PEG-CHITOSAN solution. Sonicate till complete dissolution. The formulation is spray dried with inlet temperature of 155 degree celcius to get fine nano particles in powder form.

Example 13

Dissolve 1:2 ratio of Dextran 40 kDa, PEG-20000 and folic acid in around ¾$^{th}$ quantity of 0.1% NaOH solution in water under stirring till complete dissolution. Dissolve 2:1:0.35 ratio of ceftriaxone sulbactam colistin in water. Add this mixture to the previously dissolved FA-PEG-DEXTRAN solution. The formulation is spray dried with inlet temperature of 135 degree celcius to get fine nano particles in powder form.

Example 14

Dissolve 8:1 ratio of Dextran 30 kDa, PEG-4 kDa and folic acid (FA) in around ¾$^{th}$ quantity of 0.1% NaOH solution in water under stirring for a few minutes till complete dissolution. Dissolve cefepime amikacin in 4:1 ratio in water. Add 1-arginine, potassium chloride and disodium EDTA. Add this mixture to the previously dissolved FA-PEG-DEXTRAN solution. The formulation is spray dried with inlet temperature of 170 degree celcius to get fine nanoparticles in powder form.

Example 15

Dissolve 1:1 ratio of Dextran 40 kDa, PEG-20 kDa and folic acid (FA) in around ¾$^{th}$ quantity of 0.1% NaOH solution in water under stirring for a few minutes till complete dissolution. Dissolve levofloxacin and metronidazole in 1:2 ratio in water. Add zinc sulphate. Add this mixture to the previously dissolved FA-PEG-DEXTRAN solution. The formulation is spray dried with inlet temperature of 120 degree celcius to get fine nanoparticles in powder form.

Example 16

Dissolve 1:4 ratio of Dextran 40 kDa, PEG-20 kDa and folic acid in around ¾$^{th}$ quantity of 0.1% NaOH solution in water under continuous stirring. Dissolve CoQ 10 and omega-3 fatty acids in 1:8 ratio in ethanol. Add this mixture to the previously dissolved FA-PEG-DEXTRAN solution. The formulation is spray dried with inlet temperature of 105 degree celcius to get fine nano particles in powder form.

Example 17

Dissolve 1:1 ratio of Dextran 40 kDa, PEG-20000 and n-actyl cystein (NAC) in around ¾$^{th}$ quantity of water under continuous stirring. Dissolve hypericin in ethanol. Add this mixture to the previously dissolved NAC-PEG-DEXTRAN solution. Sonicate till complete dissolution. The formulation is spray dried with inlet temperature of 170 degree celcius to get fine nano particles in powder form.

Example 18

Dissolve 5:1 ratio of Dextran 40 kDa, PEG-20 kDa and folic acid in around ¾$^{th}$ quantity of 0.1% NaOH solution in water in a beaker under continuous stirring. Dissolve mangiferin in hot dilute ethanol. Add this mixture to the previously dissolved FA-PEG-DEXTRAN solution. Sonicate till complete dissolution. The formulation is spray dried with inlet temperature of 160 degree celcius to get fine nano particles in powder form.

Example 19

Dissolve 4:1 ratio of Dextran 40 kDa, PEG-20 kDa and folic acid in around ¾$^{th}$ quantity of 0.1% NaOH solution in water in a beaker under continuous stirring. Dissolve tacrolimus in cremophor RH 60. Add this mixture to the previously dissolved FA-PEG-DEXTRAN solution. The formulation is spray dried with inlet temperature of 150 degree celcius to get fine nano particles in powder form.

Example 20

Dissolve 5:1 ratio of Dextran 40 kDa, PEG-20 kDa and folic acid in around ¾$^{th}$ quantity of 0.1% NaOH solution in water in a beaker under continuous stirring. Dissolve rabeprozole and sucralfate in mild acidic water. Add this mixture to the previously dissolved FA-PEG-DEXTRAN solution. The formulation is spray dried with inlet temperature of 155 degree celcius to get fine nano particles in powder form.

According to yet another embodiment of current invention, the ratio of therapeutic agents can be altered as per need and is not a limiting factor of invention. STN of current invention may be used for co administering PBTA with a known high bioavailable therapeutic agent and provides/offers a lot of variability and can be used for multiple formulations for varied variety of PBTA for different therapeutic uses.

According to yet another embodiment of current invention, the composition of said stealth targeted nanoparticles swell and burst when administered orally, to form smaller nanoparticles of size ≤20 nm which allow enhanced circulation without opsonization. The said smaller nanoparticles increase bioavailability of said poorly bioavailable therapeutic agent to >70%, more specifically to >90% which may result in >100% cumulative bioavailability at certain point of time in body.

STN technology of current invention and compositions made thereof provide added advantage by small size, customized surface, improved solubility, target delivery and multi-functionality.

As per yet another embodiment of current invention the major advantage is that compositions can be tailor-made to achieve both controlled drug release and disease-specific localization. It further provides targeted (cellular or tissue) delivery of poorly bioavailable therapeutic agents, improve bioavailability, sustain release of said PBTAs and make them available for systemic delivery by protecting the said therapeutic agents against enzymatic degradation using advancement in technology and green chemistry.

According to yet another embodiment, STN technology based PBTA release rate is enhanced by (1) therapeutic agent solubility; (2) desorption of the surface-bound or adsorbed therapeutic agent; (3) therapeutic agent diffusion through the nanoparticle matrix; (4) nanoparticle matrix bursting; and/or (5) combination of erosion and diffusion of nanomatrix processes. Solubility, diffusion, and biodegradation of the particle matrix govern the release process. The rapid, initial release, or 'burst', is mainly attributed to weakly bound or adsorbed therapeutic agent to the relatively large surface of STN matrix due to physical entrapment. Additionally stealth polymer matrix provides sustained effect.

According to yet another embodiment the STN technology and formulations made thereof are non lipid matrix.

According to the said another embodiment the STN technology and formulations made thereof do not form a chemical complex and are formed using green chemistry approach wherein PBTAs are trapped in inner core of non lipid polymer matrix formed by stealth polymer, polysaccharide agent trapping targeting agent using heat for cross linking, such STNs are delivered orally at specific pH where nanoparticles explode/burst to form smaller nanoparticles which allow enhanced circulation in body and significantly enhanced bioavailability of PBTAs.

According to the said embodiment STN technology allow more than 90% entrapment, more specifically entrapment efficiency is >97% of PBTA in polymer matrix.

According to the said embodiment STN technology based PBTAs achieve >70% bioavailability.

According to yet another embodiment the bioavailability of PBTAs is >90% using STN technology.

According to a preferred embodiment, stealth targeted nanoparticles (STN) of Poorly Bio-Available Therapeutic Agents (PBTAs) are formed by water evaporation/sublimation and spray drying/freeze drying method.

According to the said embodiment, the said nanoparticles are then granulated/spheronizer-extruded to get granules/multi unit particulate system (MUPS). The granules/MUPS are then enteric coated with pH dependent/sensitive polymers to get pH sensitive, stealth, targeted ligand appended semi-interpenetrating network based nanoparticles, without covalent linking, with PBTAs entrapped in non lipid inner core.

According to yet another preferred embodiment, stealth targeted nanoparticle technology has PEG 20 kDa as a stealth polymer, Dextran 40 kDa as polysaccharide agent to form polymeric backbone material and vitamin, preferably folic acid as targeting agent. All three materials are dissolved in water, to form a semi-interpenetrating network structure entrapping targeting agent. PBTAs are then dissolved in this ligand appended polymeric matrix of PEG-dextran-folic acid matrix to form therapeutic agent loaded nanoparticles. These nanoparticles are further heated at >100 degree celcius, preferably 140 degree celcius, more preferably between 120 to 170 degree celcius to harden the core polymer matrix during spray drying. Alternatively these may be freeze dried by vacuum evaporation technique/sublimation to achieve stealth targeted nanoparticles of around 1000 nm. These nanoparticles are then granulated/spheronizer-extruded to get granules/MUPS. The granules/MUPS are then enteric coated with pH dependent/sensitive polymers to get pH sensitive, stealth, targeted nanoparticles which can be in the form of tablet, capsule, sachet, or any other known oral delivery form.

According to the said preferred embodiment, the said STNs of size ≤1000 nm when delivered orally are delivered in gastro intestinal lumen, preferably intestinal lumen where after internalization these nanoparticles further swell and burst to form smaller nanoparticles of ≤20 nm size and provide >70% bioavailability of PBTAs.

According to yet another embodiment of STN technology bioavailability is enhanced to >90% due to swelling and bursting of nanoparticles aided by polysaccharide polymeric back bone which preferably is dextran ≤40 kDa. This results in >100% cumulative bioavailability at a certain point, when STN are orally administered.

According to yet another aspect of invention it provides following advantages: STN technology has a biodegradable and biocompatible polymeric-polysaccharide matrix which can encapsulate a variety of small molecule poorly bioavailable therapeutic agents inside the polymer matrix to show a controlled release profile over a period of time with >90% entrapment efficiency and >70% bioavailability.

The poly(ethylene) glycol as water soluble polymer imparts stealth property to the nanoparticles and thereby prevents opsonization (macrophagic determination) and lymphatic clearance, thereby it prolongs the circulation time of the nanoparticles in vivo.

The enteric coating imparts pH sensitive nature to the nanoparticles and thereby prevents the gastric degradation of acid labile drugs and is optional feature to achieve intestinal delivery.

The active targeting approach by using various non protein ligands such as folic acid, transferrin, anti oxidants, vitamins, biotin, cynocobalamine, hydroxylcobalamine and endogenous substance which don't have any toxic effects and is used in a very minute concentration, helps in formation of ligand appended nanoparticles to deliver the said poorly bioavailable therapeutic agent across the gastrointestinal membrane for very tough to deliver drugs with "zero" or low oral bioavailability. They can supply these highly impermeable PBTAs entrapped in non lipid matrix through the gastro-intestinal epithelium like enclosed in tiny packets due to nanometer size range and receptor mediated endocytosis.

The STN technology provides ease of administration as oral therapy in the form of sachet, granules, tablets, capsules, MUPS etc. for the said PBTAs which can not be administered through oral route earlier. This technology is beneficial for paediatric and geriatric patients (increased patient compliance due to switchover from painful parenteral therapy to oral therapy), more bioavailability leading to lesser administration of therapeutic agent and lesser side effects of drugs.

This technology reduces the amount of drugs used to kill bacterial and cancer cells & can target the other receptor based therapies. It also provides pharmacoeconomic benefits as it is cost-effective and within the reach of a common man.

Novel and innovative technology of STN to deliver highly impermeable BCS class III and IV drugs (also known as problem drugs), herbs, nutraceuticals by using stealth targeted nanoparticle technology through oral delivery by targeting intestinal folate receptors and thereby delivering the therapeutic agent to the systemic circulation and increase the oral bioavailability to >70%.

In accordance with certain aspect of the invention STN technology can deliver any poorly bioavailable therapeutic agent which is a BCS class III or IV drug or nutraceutical or other poorly bio-available therapeutic agent of natural or synthetic origin to the subject/patient for intended use by means of various formulations.

In another aspect of formulations such nanoparticles are enteric coated and can be delivered in any acceptable oral form know to a person skilled in the art.

In accordance with certain aspect of the invention STN technology can provide therapeutic effect for cancer, bacterial/fungal infections, arthritis, pain, viral infections, age related diseases, contagious diseases, orphan diseases, hereditary diseases, life style diseases, deficiency diseases, immune disorders and other nutritional support requirements by delivering said small molecule allopathic, herbal, natural therapeutic agents (PBTAs) in condition of need.

As per yet another embodiment of current invention STN technology and compositions made thereof are non toxic. Conventionally quantum dots and other nano material is reported to have high nano-toxicity and most cationic nanoparticles can cause hemolysis and blood clotting.

According to another novel aspect of the present invention, there is provided an organic solvent free process for the production of semi inter penetrating network matrix for physical entrapment of polymer matrix constituents and targeting ligand.

According to another novel aspect, the said STN are made by physical cross linking and does not involve covalent bond or conjugation and is highly stable.

According to yet another novel aspect of current invention stealth targeted nanoparticles of poorly bioavailable small molecule therapeutic agents for said therapeutic use are made with simple process using heat cross linking of water soluble polymer and polysaccharide backbone to form matrix which form semi inter penetrating network and trap a polar targeting ligand which moves to surface due to blooming effect and provides effective targeting of said therapeutic agent assisting in improving bioavailability to >70%. These nanoparticles are then water evaporated, dried, coated and filled using known techniques in orally deliverable forms. Such STNs are stable, have capacity to load high therapeutic agent concentrations, targeted delivery, bursting into smaller nanoparticles for longer systemic circulation, preventing opsonization, reducing dosing frequency, reducing adverse effects and potential to encapsulate a variety of small molecules for said therapeutic effects with varied concentrations.

According to yet another embodiment of current invention STN technology and formulations made thereof are technologically advanced and easier to manufacture, overcome another challenge, in terms of scaling up laboratory or pilot technologies for consistent and reproducible production and commercialization because conventionally up scaling for nano-drug delivery i.e; the large-scale production of nano-materials is difficult, complicated, require highly skilled manpower & machine, cumbersome and costly. A number of nano-drug delivery technologies may not be compatible with large-scale production owing to the nature of the preparation method and high cost of materials employed. The challenges of scaling up include a low concentration of nano-materials, agglomeration and the chemistry process. All these challenges are successfully overcome by current invention by selection of appropriate stealth polymer matrix along with vitamin targeting for efficient delivery of therapeutic agents without complicating the manufacturing process.

What is claimed is:

1. A composition for targeted delivery of poorly bioavailable therapeutic agents comprising of stealth targeted nanoparticles, wherein said stealth targeted nanoparticles comprise of:
   i) a non-lipidic polymer matrix, comprising of at least one stealth polymer and at least one polysaccharide;
   ii) a non-protein targeting agent/ligand; and
   iii) one or more than one poorly bioavailable therapeutic agent,
   wherein
   said non-protein targeting agent/ligand is a vitamin in a range of 0.01 mg to 10 mg and said at least one stealth polymer is selected from the group consisting of polyethylene glycol (PEG), PEG-based copolymers, PEG derivatives, and PEG-2000 to 20000;
   wherein said non-lipidic polymer matrix and non-protein targeting agent/ligand together form a ligand-appended polymer matrix, wherein the ratio of said one or more than one poorly bioavailable therapeutic agent to said ligand-appended polymer matrix is 1:1 to 1:10;
   the weight ratio of said at least one stealth polymer to said at least one polysaccharide is 1:10 to 1:1;
   said non-protein targeting agent/ligand and said one or more than one poorly bioavailable therapeutic agent are physically entrapped inside the non-lipidic polymer matrix without conjugation or covalent bonding to form stable, stealth targeted nanoparticles of size <1000 nm;
   the composition of said stealth targeted nanoparticles, when administered, form smaller nanoparticles of size <20 nm;
   said smaller nanoparticles increase bioavailability of said one or more than one poorly bioavailable therapeutic agent by 70-90%;
   said composition is suitable for oral administration to a subject in need thereof.

2. The composition of claim 1, wherein said at least one polysaccharide is dextran.

3. The composition of claim 1, wherein the non-protein targeting agent/ligand is folic acid.

4. The composition of claim 1 wherein the said non-protein targeting agent/ligand is polar, wherein the non-protein targeting agent/ligand is capable of moving to a surface of the nanoparticle due to blooming.

5. The composition of claim 1, wherein the one or more than one poorly bioavailable therapeutic agent is selected from the group consisting of a drug, a nutraceutical, a diagnostic agent, a salt thereof, an isomer thereof, a derivative thereof, and a mixture thereof.

6. The composition of claim 5, wherein the drug is a small molecule selected from the group consisting of antibiotics, antivirals, anti osteoporosis drugs, anti arrhythmic drugs, ACE inhibitors, antihistamines, anticancer drugs, anti fungal drugs, diuretics, anthelmintics, anti-tubercular drugs, anti-rheumatoid drugs, anti-ulcer drugs, immunosuppressants, BCS class III drugs, BCS class IV drugs, and mixture thereof.

7. The composition of claim 5, wherein the drug is an antibiotic alone or in a combination with beta-lactamase inhibitor, polymixin, sulphonamides, tetracyclines, aminoglycosides, lincosamides, streptogramins, ketolides, glycylcyclines, phenicols, oxazolidinones, ansamycins, glycopeptide, lipopeptides, cyclic lipopeptides, fluoroquinolones, imidazole, fosfomycins, oxalidinones, macrolides, anti metabolites, furanes, and pharmaceutically acceptable salts, isomers and derivative thereof, wherein the antibiotic is a beta lactam antibiotic and is selected from the group consisting of cephalosporins, carbapenems, cephamycin, monobactams and penicillins.

8. The composition of claim 7, wherein the cephalosporin drug is ceftriaxone.

9. The composition of claim 7, wherein the drug is a combination of beta lactam antibiotic and one or more of co-drug beta lactamase inhibitors, wherein the said beta-lactam antibiotic is selected from the group consisting of ceftriaxone, cefepime, ceftazidime, cefuroxime, cefexime, cefpodoxime, cefaclor, cefoperazone, cefadroxil, ceftibuten, cefdinir, cefditoren, ceftizoxime, cefamandole, cefazolin, cefonicid, cefoxitin, cefprozil, cephalexin, cephapirin, ceftobiprole, ceftolozane, ceftaroline, cephradine, and pharmaceutically acceptable salts thereof and the said co-drug beta-lactamase inhibitor is selected from the group consisting of sulbactam, tazobactam, clavulanic acid, avibactam, relebactam, RPX709, NXL104, AVE1330A, and pharmaceutically acceptable salts, isomers, and derivatives thereof.

10. The composition of claim 7, wherein the drug is a combination of carbapenem antibiotic and one or more of beta lactamase inhibitors, wherein the said carbapenem drug is selected from the group consisting of meropenem, etrapenem, doripenem, panipenem, tebipenem, sanfetrinem, tomopenem, biapenem, and pharmaceutically acceptable salts thereof and the said beta-lactamase inhibitor is selected from the group consisting of sulbactam, tazobactam, clavulanic acid, avibactam, relebactam, RPX709, NXL104, AVE1330A, and pharmaceutically acceptable salts, isomers, and derivatives thereof.

11. The composition of claim 7, wherein the drug is a combination of carbapenem antibiotic and one or more second antibiotic drugs whose mechanism of killing bacteria is different from that of carbapenems, wherein the said carbapenem drug is selected from the group consisting of meropenem, doripenem, ertapenem, panipenem, tebipenem, sanfetrinem, tomopenem, biapenem, and pharmaceutically acceptable salts thereof and the said one or more second antibiotic drugs is selected from the group consisting of aminoglycoside, glycopeptide, lipopeptide, polymixin, quinolone, imidazole, a prodrug thereof, and pharmaceutically acceptable salts, isomers, and derivatives thereof.

12. The composition of claim 7, wherein the drug is a combination of cephalosporin antibiotic and one or more second antibiotic drugs whose mechanism of killing bacteria is different from that of cephalosporins, wherein the said cephalosporin drug is selected from the group consisting of ceftriaxone, cefepime, ceftazidime, cefuroxime, cefexime, cefpodoxime, cefaclor, cefoperazone, cefadroxil, ceftibuten, cefdinir, cefditoren, ceftizoxime, cefamandole, cefazolin, cefonicid, cefoxitin, cefprozil, cephalexin, cephapirin, ceftobiprole, ceftolozane, ceftaroline, cephradine, and pharmaceutically acceptable salts thereof and the said one or more second antibiotic drug is selected from the group consisting of aminoglycoside, glycopeptide, lipopeptide, polymixin, quinolone, imidazole, a prodrug thereof, and pharmaceutically acceptable salts, isomers, and derivatives thereof.

13. The composition of claim 6, wherein the drug is an anticancer drug selected from the group consisting of cisplatin, carboplatin, oxaliplatin, mechlorethamine, cyclophosphamide, chlorambucil, ifosfamide, plant alkaloids selected from the group consisting of vincristine, vinblastine, vinorelbine, vindesine, podophyllotoxins selected from the group consisting of etoposide and teniposide, taxanes selected from the group consisting of docetaxel, paclitaxel, topoisomerase inhibitors selected from the group consisting of irinotecan and topotecan, cytotoxic antibiotics selected from the group consisting of actinomycin, anthracyclines, doxorubicin, dactinomycin, cytarabine, bortezomib, gemcitabine, daunorubicin, valrubicin, idarubicin, epirubicin, bleomycin, fludarabine, clatribine, methotrexate, 5-flurouracil, amscrine, cladribine, carmustine plicamycin, mitomycin, pemetrexate capecitabine, dasatinib, erlotinib, fludarabine, imatinib, lapatinib, nilotinib, sorafenib, sunitinib, thalidomide, 9-nitrocamptothecin, curcumin, exemestane, mitotane, raloxifene, emodin, methotrexate, tamoxifen, benzyl isothiocyanate, melphalan, mesotetraphenylporphine, a-mangostin, quercetin, epigallocatechin gallate, 10-hydroxycamptothecin, thymopentin, rapamycin, altretamine, anagrelide, anastrazole, bexarotene, bicalutamide, finasteride, gefitinib, hydroxycarbamide, ibandronic acid, imatinib, lapatinib, lenalidomide, letrozole, mercaptopurine, nilutamide, procarbazine, raloxifene, rubitecan, sobuzoxane, sunitinib, tamibarotene, tamoxifen, temozolomide, thalidomide, thioguanine, toremifene, treosulfan, vorinostat, and pharmaceutically acceptable salts, isomers, and derivatives thereof.

14. The pharmaceutical composition of claim 6, wherein the drug is an immunosuppressant selected from the group consisting of azathioprine, cyclosporine, daclizumab, mycophenolate mofetil prednisone, sirolimus, tacrolimus, everolimus, basiliximab muromonab CD3, and pharmaceutically acceptable salts, isomers, and derivatives thereof.

15. The composition of claim 6, wherein the drug is an anti inflammatory selected from the group consisting of celecoxib, diclofenac, diflunisal, etodolac fenoprofen, flurbiprofen, ibuprofen, indomethacin, ketoprofen, ketorolac, meloxicam, nabumetone, naproxen, oxaprozin, piroxicam, salsalate, sulindac, tolmetin, and pharmaceutically acceptable salts, isomers, and derivative thereof.

16. The composition of claim 5, wherein said nutraceutical is selected from the group consisting of vitamins, antioxidants, dietary minerals, essential elements, proteins, herbal extracts, and herbal supplements.

17. The composition of claim 1, wherein said at least one stealth polymer is PEG, said at least one polysaccharide is dextran, said one or more than one poorly bioavailable therapeutic agent is a drug or nutraceutical, said weight ratio of PEG to Dextran is 1:10 to 1:1, and said nanoparticles swell and burst after oral administration to form smaller nanoparticles of size <20 nm to improve cumulative bioavailability to >100% of said therapeutic agent.

18. A method of preparing the composition of claim 1, said method comprising the steps of:
  i. preparing a semi-inter-penetrating-network of the at least one stealth polymer, the at least one polysaccharide, and the non-protein targeting agent/ligand by dissolving said at least one stealth polymer and said at least one polysaccharide in a fixed weight ratio with said non-protein targeting agent/ligand in aqueous solution;
  ii. adding the said poorly bioavailable therapeutic agent or a mixture of poorly bioavailable therapeutic agents to said semi inter penetrating network and mixing under inert atmosphere for a few minutes to form a clear solution;
  iii. heating said solution to between 120 and 170 degrees celcius to harden the polymer matrix during spray drying to obtain stealth targeted nanoparticles of size <1000 nm.

19. The composition of claim 1, wherein said stealth targeted nanoparticles target intestinal receptors.

* * * * *